(12) United States Patent
Mougin

(10) Patent No.: US 6,692,733 B1
(45) Date of Patent: *Feb. 17, 2004

(54) COMPOSITION COMPRISING POLYMERS HAVING A STAR STRUCTURE, THE POLYMERS, AND THEIR USE

(75) Inventor: Nathalie Mougin, Paris (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/544,394

(22) Filed: Apr. 5, 2000

(30) Foreign Application Priority Data

Apr. 6, 1999 (FR) .............................. 99 4256

(51) Int. Cl.$^7$ ......................... A61K 31/74; A61K 6/00; A61K 7/00; A61K 7/06; A61K 7/11
(52) U.S. Cl. ................ 424/78.18; 424/401; 424/70.11; 514/880; 526/72; 526/73; 526/319; 525/64; 525/163; 525/222; 525/299; 525/314
(58) Field of Search .............................. 424/401, 78.03, 424/78.18, 70.11; 526/72, 73, 319; 514/880; 525/64, 163, 222, 299, 314

(56) References Cited

U.S. PATENT DOCUMENTS

| | | | |
|---|---|---|---|
| 3,907,984 A | | 9/1975 | Calvert et al. ................ 424/47 |
| 4,659,783 A | | 4/1987 | Spinelli ....................... 525/293 |
| 5,221,534 A | * | 6/1993 | DesLauriers et al. .... 424/78.03 |
| 5,310,807 A | | 5/1994 | Antonelli et al. ............ 525/286 |
| 5,362,813 A | * | 11/1994 | Antonelli et al. ........... 525/286 |
| 5,371,147 A | | 12/1994 | Spinelli et al. .............. 525/288 |
| 5,527,524 A | * | 6/1996 | Toalia et al. ................ 424/1.33 |
| 5,552,491 A | | 9/1996 | Mishra et al. ............... 525/299 |
| 5,804,664 A | | 9/1998 | Kennedy et al. |
| 5,807,937 A | * | 9/1998 | Matyjaszewski et al. ... 526/111 |
| 5,849,278 A | | 12/1998 | Piot et al. ................... 424/70.7 |
| 5,919,442 A | * | 7/1999 | Yin et al. ................. 424/78.18 |
| 5,986,020 A | * | 11/1999 | Campbell et al. ............. 526/64 |
| 6,001,342 A | * | 12/1999 | Forestier et al. ............ 424/76.1 |
| 6,013,735 A | | 1/2000 | Mishra et al. ............... 525/299 |
| 6,024,948 A | * | 2/2000 | Samain et al. ........... 424/70.16 |
| 6,090,902 A | * | 7/2000 | Kuo et al. ................... 526/279 |
| 6,113,882 A | * | 9/2000 | Mougin et al. ................ 424/47 |
| 6,124,411 A | * | 9/2000 | Matyjaszewski et al. ... 526/111 |
| 6,132,736 A | | 10/2000 | Mellul et al. ................ 424/401 |
| 6,139,827 A | | 10/2000 | Cohen et al. .................. 424/16 |
| 6,150,468 A | * | 11/2000 | Schoenberg et al. ........ 525/222 |
| 6,476,124 B1 | | 11/2002 | Mougin ........................ 525/64 |

FOREIGN PATENT DOCUMENTS

| | | |
|---|---|---|
| DE | 43 28 004 | 2/1995 |
| DE | 196 02 540 | 7/1997 |
| EP | 0 557 196 | 8/1993 |
| EP | 0 639 371 | 2/1995 |
| WO | WO 86/00626 | 1/1986 |
| WO | WO 96/33690 | 10/1996 |
| WO | WO 96/36323 | 11/1996 |
| WO | WO 97/18247 | 5/1997 |

OTHER PUBLICATIONS

Co-pending Application No. 10/139,530; Attorney Docket No. 05725.0564–01 Title: Composition Comprising Polymers Having a Star Structure, the Polymers, and Their Use Inventors: Nathalie Mougin U.S. Filing Date: May 7, 2002.
Co-pending Application No. 10/345,977; Attorney Docket No. 05725.0565–01 Title: Composition Comprising Polymers Having a Star Structure, the Polymers, and Their Use Inventors: Nathalie Mougin U.S. Filing Date: Jan. 17, 2003.
Co-pending Application No. 10/247,362; Attorney Docket No. 05725.0571–01 Title: Composition Comprising Polymers Having a Star Structure, the Polymers, and Their Use Inventors: Nathalie Mougin U.S. Filing Date: Sep. 20, 2002.
Co-pending Application No. 09/543,778; Attorney Docket No. 05725.0565 Title: Composition Comprising Polymers Having a Star Structure, the Polymers, and Their Use Inventors: Nathalie Mougin U.S. Filing Date: Apr. 5, 2000.
Co-pending Application No. 09/544,655; Attorney Docket No. 05725.0570 Title: Composition Comprising Polymers Having a Star Structure, the Polymers, and Their Use Inventors: Nathalie Mougin U.S. Filing Date: Apr. 5, 2000.
Co-pending Application No. 09/543,935; Attorney Docket No. 05725.0571 Title: Composition Comprising Polymers Having a Star Structure, the Polymers, and Their Use Inventors: Nathalie Mougin U.S. Filing Date: Apr 5, 2000 (now U.S. Pat. No. 6,476,124).
Co-pending Application No. 09/544,397; Attorney Docket No. 05725.0564 Title: Composition Comprising Polymers Having a Star Structure, the Polymers, and Their Use Inventors: Nathalie Mougin U.S. Filing Date: Apr. 5, 2000 (now Abandoned).
English language esp@cent Abstract of EP 0 557196.
English language esp@cent Abstract of EP 0 639 371.
"Polymer Chemistry", second edition, 1988 Seymour et al. Mercel Dekker, Inc., pp. 354–358.
"Polymer Handbook" third edition, 1972 John Willey and Sons, Brandrup et al., pp. 11–193.
Product Information for Styrolux 684D (Sep. 1998) available from the BASF Company at www.basf.de (last checked Apr. 1, 2002).
Seiya Kobatake et al., "Synthesis of Nitroxy–Functionalized Polybutadiene by Anionic Polymerization Using a Nitroxy––Functionalized Terminator", Macromolecules, vol. 30, No. 14, Jul. 14, 1997, pp. 4238–4241.
English language Derwent Abstract of DE 43 28 004.
English language Derwent Abstract of DE 196 02 540.

* cited by examiner

*Primary Examiner*—Sreeni Padmanabhan
*Assistant Examiner*—Lauren Q. Wells
(74) *Attorney, Agent, or Firm*—Finnegan, Henderson, Farabow, Garrett & Dunner, L.L.P.

(57) ABSTRACT

A composition, comprising, in a physiologically acceptable medium, at least one polymer with a highly specific ordered structure is disclosed. These compositions find a specific application in the field of caring for the skin, in particular of the face, and more especially for treating, that is to say decreasing, erasing and/or smoothing out, wrinkles and/or fine lines of the skin.

8 Claims, No Drawings

COMPOSITION COMPRISING POLYMERS HAVING A STAR STRUCTURE, THE POLYMERS, AND THEIR USE

The present invention relates to a composition, in particular a cosmetic composition, comprising, in a physiologically acceptable medium, at least one polymer with a highly specific ordered structure. These compositions find a specific application in the field of caring for the skin, in particular of the face, and more especially for treating, that is to say decreasing, erasing and/or smoothing out, wrinkles and/or fine lines of the skin of human beings.

During the ageing process, various characteristic signs appear on the skin, such as the appearance of fine lines and/or wrinkles, which increase with age. A disruption of the "grain" of the skin is in particular observed, that is to say that the microrelief is less uniform and exhibits an anisotropic nature.

It is known to treat these signs of ageing by using compositions comprising active principles capable of combating ageing, such as α-hydroxy acids, β-hydroxy acids and retinoids. These active principles act on the wrinkles by removing dead cells from the skin and by accelerating the process of cell replacement. However, these active principles exhibit the disadvantage of only being effective in the treatment of wrinkles after a certain application time.

In point of fact, attempts are increasingly being made to obtain an immediate effect, resulting rapidly in the smoothing out of the wrinkles and/or fine lines and in the disappearance, even temporary, of the signs of tiredness.

Provision has then in particular been made to use an aqueous dispersion of polymer particles as tightening agent for the skin, resulting in the wrinkles being concealed by smoothing out the skin.

However, these compositions are still provided in the aqueous form, which can result, on the one hand, in bacteriological problems and especially, on the other hand, in excessively easy removal of the make-up in the presence of water. This is because it is impossible, with this solution, to prepare a composition exhibiting good persistence to water.

Applicant has found that, surprisingly and unexpectedly, the use of highly specific polymers exhibiting a specific ordered structure can make it possible to obtain a composition capable of being applied to the skin which can make it possible to improve the "concealing" and/or to soften the wrinkles and/or fine lines already formed.

This is because the polymers employed in the present invention have well determined physical characteristics and constitute particularly effective tightening agents. The term "tightening agent" is understood to mean compounds capable of having a tightening effect, that is to say which can tighten the skin and, by this tightness effect, smooth out the skin and cause the wrinkles and fine lines thereon immediately to decrease, indeed even to disappear.

Furthermore, the compositions thus obtained exhibit a good persistence to water.

Thus, a subject-matter of the present invention is a polymer with a "star" structure represented by the following formula (I):

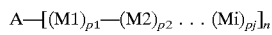

in which:
A represents a polyfunctional centre, with a functionality of "n", n being an integer greater than or equal to 2,
$[(M1)_{p1}—(M2)_{p2} \ldots (Mi)_{pj}]$ represents a polymer chain, also known as a "branch", composed of identical or different polymerized monomers Mi having a polymerization index pj, each branch being identical or different and being grafted covalently to the centre A;
i being greater than or equal to 1 and pj being greater than or equal to 2;
the polymer comprising one or more monomers Mi chosen from polymerized monomers Mk, which may be identical or different, wherein a homopolymer formed by the corresponding polymerized monomers Mk has a Tg of greater than or equal to approximately 10° C., preferably of greater than or equal to 15° C and even better still of greater than or equal to 20° C.

In a preferred embodiment, this or these monomers Mk being present, in the final polymer, in a minimum amount of approximately 45% by weight, preferably in an amount of between 55 and 99% by weight and even better still in an amount of 75–90% by weight with respect to the total weight of monomers.

Another subject-matter of the present invention is a polymer as described above further comprising one or more monomers Mj, the corresponding homopolymer of which exhibits a Tg of less than or equal to approximately 10° C., preferably of less than or equal to 5° C. and even better still of less than or equal to 0° C.

In a preferred embodiment, this or these monomers Mj are present in the final polymer in a maximum amount of approximately 55% by weight, preferably in an amount of between 1 and 45% by weight and even better still in an amount of 10–25% by weight with respect to the total weight of monomers.

Another subject-matter of the invention is a composition comprising, in a physiologically acceptable medium, at least one polymer as above.

Another subject-matter of the invention is a process for the cosmetic treatment of the skin of the face, neck, hands and/or body, characterized in that it comprises applying, to the latter, a cosmetic composition as above.

Another subject-matter of the invention is a process for the cosmetic treatment of wrinkled skin which comprises applying, to the latter, a cosmetic composition as above in an amount which is effective in softening the wrinkle or the fine line by a tightening effect.

Another subject-matter of the invention is the use of at least one polymer as above, in a cosmetic composition or for the preparation of a pharmaceutical composition, for decreasing, erasing, concealing and/or softening wrinkles and/or fine lines of the skin.

The compositions according to the invention exhibit a light texture and are very comfortable to wear throughout the day. They make it possible to obtain a film with very good hold which is soft, supple, elastic and flexible on the skin; it follows the movements of the substrate on which it is deposited, without cracking and/or detaching. In particular, it adheres perfectly to the skin of the face.

The compositions according to the invention can be readily applied and spread easily. They make it possible immediately after application to soften the wrinkles and fine lines at the surface of the skin.

The compositions of the invention can be applied in particular to the face and/or to the neck, in particular to the bare neck and shoulders.

The compositions can be easily removed, for example using a conventional make-up remover, in particular one with an oily base.

The composition according to the invention therefore comprises a polymer, the "star" structure of which can be illustrated, in a general way, by the following formula (I):

$$A\text{—}[(M1)_{p1}\text{—}(M2)_{p2}\ldots(Mi)_{pj}]_n$$

in which:

A represents a polyfunctional centre, with a functionality of "n", n being an integer greater than or equal to 2, preferably of between 4 and 10, $[(M1)_{p1}\text{—}(M2)_{p2}\ldots(Mi)_{pj}]$ represents a polymeric chain, also known as a "branch", composed of identical or different polymerized monomers Mi having a polymerization index pj, each branch being identical or different and being grafted covalently to the centre A;

i being greater than or equal to 1, preferably of between 2 and 10;

pj being greater than or equal to 2, preferably of between 10 and 20,000.

The polymer chains are preferably provided in the form of blocks with a molecular mass of greater than or equal to 500 which can range up to 2,000,000.

In a preferred embodiment, the polymer used in the context of the present invention can be obtained by controlled radical polymerization, also known as "living" radical polymerization. This technique makes it possible in particular to overcome the limitations inherent in conventional radical polymerization, that is to say that it makes it possible in particular to control the length of the chains of the polymer which is formed and therefore to obtain block structures.

The controlled radical polymerization makes it possible to reduce the reactions in which the growing radical species is deactivated, in particular the termination stage, which reactions, in conventional radical polymerization, interrupt the growth of the polymer chain in an irreversible and uncontrolled way.

In order to decrease the probability of termination reactions, provision has been made to block, in a temporary and reversible way, the growing radical species by forming so-called "dormant" active species with the aid of a bond of low dissociation energy.

In particular, mention may be made of the possibility of using bonds of C—ONR type (by reaction with a nitroxyl); this is illustrated in particular by the article "Synthesis of nitroxy-functionalized polybutadiene by anionic polymerization using a nitroxy-functionalized terminator", published in Macromolecules, 1997, volume 30, pp. 4238–4242.

Mention may also be made of the possibility of using bonds of C-halide type (in the presence of metal/ligand complex). This is then described as atom transfer radical polymerization, also known under the abbreviation ATRP. This type of polymerization is reflected in control of the mass of the polymers which are formed and in a low polydispersity index by weight of the chains.

Atom transfer radical polymerization is generally carried out by polymerization:

of one or more radically polymerizable monomers, in the presence of an initiator having at least one radically transferable atom or group, of a compound comprising a transition metal capable of participating in a reduction stage with the initiator and a "dormant" polymer chain, and of a ligand, which can be chosen from compounds comprising a nitrogen (N), oxygen (O), phosphorus (P) or sulphur (S) atom, which compounds are capable from compounds comprising a carbon atom, which compounds are capable of coordinating via a π or σ bond to the compound comprising a transition metal, the formation of direct bonds between the compound comprising a transition metal and the polymer in the course of formation being avoided.

This process is illustrated in particular in Application WO97/18247, the teaching of which can be drawn upon by a person skilled in the art in preparing the polymers coming within the scope of the present invention.

The nature and the amount of the monomers, initiator(s), compound(s) comprising the transition metal and ligand(s) will be chosen by a person skilled in the art on the basis of his overall knowledge, according to the result desired.

In particular, the monomers "M" (Mi, Mk, and Mj) can be chosen, alone or as a mixture, from radically polymerizable compounds comprising ethylenic unsaturation corresponding to the formula:

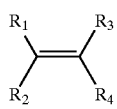

in which $R_1$, $R_2$, $R_3$ and $R_4$ are, independently of one another, chosen from:

a hydrogen atom;

a halogen atom;

a linear or branched alkyl radical having 1 to 20, preferably 1–6, more preferably 1–4, carbon atoms which is optionally substituted by one or more halogens and/or one or more —OH radicals;

a linear or branched alkenyl or alkynyl radical having 2 to 10, preferably 2–6, more preferably 2–4, carbon atoms which is optionally substituted by one or more halogens;

a cyclic hydrocarbonaceous (cycloalkyl) radical having 3 to 8 carbon atoms which is optionally substituted by one or more halogen, nitrogen, sulphur or oxygen atoms;

a radical chosen from CN, $C(=Y)R^5$, $C(=Y)NR^6R^7$, $YC(=Y)R^5$, cyclic $NC(=Y)R^5$, $SOR^5$, $SO_2R^5$, $OSO_2R^5$, $NR^8SO_2R^5$, $PR^5{}_2$, $P(=Y)R^5{}_2$, $YPR^5{}_2$, $YP(=Y)R^5{}_2$, $NR^8{}_2$, which can be quaternized with an additional $R^8$ group, aryl and heterocyclyl, with:

Y represents O, S or $NR^8$ (preferably O), $R^5$ represents a linear or branched alkyl, alkylthio or alkoxy radical having 1–20 carbon atoms; an OH radical; an OM' radical with M'=alkali metal; an aryloxy radical or a heterocyclyloxy radical;

$R^6$ and $R^7$ represent, independently of one another, H or a linear or branched alkyl radical having 1–20 carbon atoms; it being given that $R^6$ and $R^7$ can be joined to form an alkylene group having 2–7, preferably 2–5, carbon atoms;

$R^8$ represents H, a linear or branched alkyl radical having 1–20 carbon atoms or an aryl radical;

a —COOR radical, in which R is a linear or branched alkyl radical having 1 to 20, preferably 1–6, carbon atoms which is optionally substituted by one or more halogens;

a —CONHR' radical, in which R' is hydrogen or a saturated or unsaturated, linear or branched, hydrocarbonaceous radical having 1 to 20, preferably 1–6, carbon atoms which is optionally substituted by one or more halogens, nitrogens and/or oxygens;

an —OCOR" radical, in which R" is hydrogen or a saturated or unsaturated, linear or branched, hydrocarbonaceous radical having 1 to 20 carbon atoms which is optionally substituted by one or more halogens, nitrogens and/or oxygens;

a radical comprising at least one silicon atom and in particular radicals such as: an —R-siloxane radical, a —CONHR-siloxane radical, a —COOR-siloxane radical or an —OCO—R-siloxane radical, in which radicals R is a linear or branched alkyl, alkylthio, alkoxy, aryloxy or heterocycloxy radical having 1–20 carbon atoms.

The term "siloxane" is understood to mean a compound comprising $(-SiR^aR^bO-)_n$ units, in which units $R^a$ and $R^b$ can represent, independently of one another, a hydrogen; a halogen; a saturated or unsaturated, linear or branched, hydrocarbonaceous radical having 1 to 36 carbon atoms which is optionally substituted by one or more halogens, nitrogens and/or oxygens; or a cyclic hydrocarbonaceous radical having 1 to 20 carbon atoms; n being greater than or equal to 1.

For the purpose of this invention, the term "independent," when used to describe the relationship of radicals, atoms, substituents, functional groups, etc., means that each of the radicals, atoms, substituents, functional groups, etc. may be the same or different from the other, or some radicals, atoms, substituents, functional groups, etc., may be the same while the others may be different.

Mention may in particular be made of polydimethylsiloxanes (PDMSs) comprising 1 to 200, preferably less than 100, repeat units.

Furthermore, $R^1$ and $R^3$ can be connected to one another so as to form a ring of formula $(CH_2)_n$ which can be substituted by one or more halogens and/or oxygens and/or nitrogens and/or by alkyl radicals having 1 to 6 carbon atoms.

The term "aryl" or "heterocyclyl" is understood to mean the definition commonly understood by a person skilled in the art and which may be illustrated by the prior art WO97/18247.

Preferably, the monomers M can be chosen from:

acrylic or methacrylic esters obtained from linear, branched or cyclic aliphatic alcohols and/or from aromatic alcohols, preferably $C_1$–$C_{20}$ alcohols, such as methyl(meth)acrylate, ethyl(meth)acrylate, propyl(meth)acrylate, butyl(meth)acrylate, isobutyl(meth)acrylate or tert-butyl(meth)acrylate;

$C_1$–$C_4$ hydroxyalkyl(meth)acrylates, such as 2-hydroxyethyl(meth)acrylate or 2-hydroxypropyl(meth)acrylate;

ethylene glycol, diethylene glycol or polyethylene glycol (meth)acrylates with a hydroxyl or ether end;

vinyl, allyl or methallyl esters obtained from linear or branched $C_1$–$C_{10}$ or cyclic $C_1$–$C_6$ aliphatic alcohols and/or from aromatic alcohols, preferably $C_1$–$C_6$ alcohols, such as vinyl acetate, vinyl propionate, vinyl benzoate or vinyl tert-butylbenzoate;

N-vinylpyrrolidone; vinylcaprolactam; vinyl-N-alkylpyrroles having 1 to 6 carbon atoms; vinyloxazoles; vinylthiazoles; vinylpyrimidines; vinylimidazoles; and vinyl ketones;

(meth)acrylamides obtained from linear, branched or cyclic aliphatic amines and/or from aromatic amines, preferably $C_1$–$C_{20}$ amines, such as tert-butylacrylamide; and (meth)acrylamides, such as acrylamide, methacrylamide or di($C_1$–$C_4$)alkyl(meth)acrylamides;

olefins, such as ethylene, propylene, styrene or substituted styrene;

fluorinated or perfluorinated acrylic or vinyl monomers, in particular (meth)acrylic esters with perfluoroalkyl units;

monomers comprising an amine functional group in the free or else partially or completely neutralized or else partially or completely quaternized form, such as dimethylaminoethyl(meth)acrylate, dimethylaminoethylmethacrylamide, vinylamine, vinylpyridine or diallyldimethylammonium chloride;

carboxybetaines or sulphobetaines obtained by partial or complete quaternization of monomers comprising ethylenic unsaturation comprising an amine functional group by sodium salts of carboxylic acids comprising a mobile halide (sodium chloroacetate, for example) or by cyclic sulphones (propane sulphone);

silicone-comprising (meth)acrylates or (meth)acrylamides, in particular (meth)acrylic esters comprising siloxane units;

their mixtures.

The particularly preferred monomers are chosen from:

(meth)acrylic esters obtained from linear or branched aliphatic alcohols, preferably $C_1$–$C_{20}$ alcohols;

$C_1$–$C_{20}$ (meth)acrylic esters comprising perfluoroalkyl units;

$C_1$–$C_{20}$ (meth)acrylic esters comprising siloxane units;

(meth)acrylamides obtained from linear, branched or cyclic aliphatic amines and/or from aromatic amines, preferably $C_1$–$C_{20}$ amines, such as tert-butylacrylamide; or (meth)acrylamides, such as acrylamide, methacrylamide or di($C_1$–$C_4$)alkyl(meth)acrylamides;

vinyl, allyl or methallyl esters obtained from linear or branched $C_1$–$C_{10}$ or cyclic $C_1$–$C_6$ aliphatic alcohols;

vinylcaprolactam;

optionally substituted styrene;

their mixtures.

In the context of the present invention, the initiator can be any compound, in particular a molecular or polymeric compound, having at least two atoms and/or groups which are radically transferable by polymerization.

The initiator can in particular be an oligomer or a polymer capable of being obtained by radical polymerization, by polycondensation, by anionic or cationic polymerization or by ring opening.

The transferable atoms and/or groups can be situated at the ends of the polymer chain or along the backbone.

Mention may in particular be made of the compounds corresponding to one of the following formulae:

$$-R^{11}CO-X$$

$R^{11}{}_xR^{12}{}_yR^{13}{}_zC-(RX)_t$, in which x, y and z represent an integer ranging from 0 to 4, t an integer ranging from 1 to 4, and x+y+z=4−t;

$R^{13}{}_xC_6-(RX)_y$ 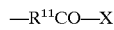 (saturated ring with 6 carbons), in which x represents an integer ranging from 7 to 11, y represents an integer ranging from 1 to 5, and x+y=12;

$R^{13}{}_xC_6-(RX)_y$ (unsaturated ring with 6 carbons), in which x represents an integer ranging from 0 to 5, y represents an integer ranging from 1 to 6, and x+y=6;

$-[-(R^{11})(R^{12})(R^{13})C-(RX)-]_n$, in which n is greater than or equal to 1; cyclic or linear;

$-[-(R^{12})_xC_6(RX)_y-R^{11}-]_n$, in which x represents an integer ranging from 0 to 6, y represents an integer ranging from 1 to 6 and n is greater than or equal to 1, with x+y=4 or 6; cyclic or linear;

—[—$(R^{12})_xC_6(RX)_y$—$R^{11}$—]$_n$, in which x represents an integer ranging from 0 to 12, y represents an integer ranging from 1 to 12 and n is greater than or equal to 1, with x+y=10 or 12; cyclic or linear;

$$R^{11}R^{12}R^{13}Si—X$$

—[OSi$(R^{11})_x(RX)_y$]$_n$, cyclic or linear, in which x and y represent an integer ranging from 0 to 2 and n is greater than or equal to 1, with x+y=2;

$$R^{11}R^{12}N—X$$

$$R^{11}N—X_2$$

$(R^{11})_xP(O)_y$—$X_{3-x}$, in which x and y represent integers ranging from 0 to 2 and x+y=5;

$(R^{11}O)_xP(O)y$—$X_{3-x}$, in which x and y represent integers ranging from 0 to 2 and x+y=5;

—[$(R^{11})_tN_zP(O)_x(O$—$RX)_y$—]$_n$, cyclic or linear, in which x represents an integer ranging from 0 to 4, y represents an integer ranging from 1 to 5, z represents an integer ranging from 0 to 2, t represents an integer ranging from 0 to 3 and n is greater than or equal to 1;

in which:
R, $R^{11}$, $R^{12}$ and $R^{13}$ represent, independently of one another, a hydrogen or halogen atom; a linear or branched alkyl radical having 1–20, preferably 1–10 and more preferably 1–6 carbon atoms; a cycloalkyl radical having 3–8 carbon atoms; a —C(=Y)$R^5$, —C(=Y)NR$^6$R$^7$ or —R$^8_3$Si radical (see the definitions of $R^5$ to $R^8$ above); —COCl; —OH; —CN; an alkenyl or alkynyl radical having 2–20, preferably 2–6, carbon atoms; an oxiranyl or glycidyl radical or an alkylene or alkenylene radical substituted with an oxiranyl or a glycidyl; an aryl, heterocyclyl, aralkyl or aralkenyl radical; or an alkyl radical having 1–6 carbon atoms in which all or part of the hydrogen atoms are substituted either by halogen atoms, such as fluorine, chlorine or bromine, or by an alkoxy group having 1–4 carbon atoms or by an aryl, heterocyclyl, —C(=Y)$R^5$, —C(=Y)NR$^6$R$^7$, oxiranyl or glycidyl radical;

X represents a halogen atom, such as Cl, Br or I, or an —OR', —SR, —SeR, —OC(=O)R', —OP(=O)R', —OP(=O)(OR')$_2$, —OP(=O)OR', —O—NR'$_2$, —S—C(=S)NR'$_2$, —CN, —NC, —SCN, —CNS, —OCN, —CNO and —N$_3$ radical, in which R' represents an alkyl radical having 1–20 carbon atoms which is optionally substituted by one or more halogen atoms, in particular fluorine and/or chlorine atoms, and R represents a linear or branched alkyl or aryl radical having 1–20, preferably 1–10, carbon atoms, it additionally being possible for the —NR'$_2$ group to represent a cyclic group, the two R' groups being joined so as to form a 5-, 6- or 7-membered heterocycle.

Preferably, X represents a halogen atom and in particular a chlorine or bromine atom.

The initiator is preferably chosen from the compounds of formula $R^{13}_xC_6$—$(RX)_y$ (saturated ring with 6 carbons) in which x represents an integer ranging from 7 to 11, y represents an integer ranging from 1 to 5 and x+y=12;

—[—$(R^{12})_xC_6(RX)_y$—$R^{11}$—]$_n$, in which x represent an integer ranging from 0 to 6, y represents an integer ranging from 1 to 6 and n is greater than or equal to 1, with x+y=4 or 6; cyclic or linear; and —[OSi$(R^{11})_x(RX)_y$]$_n$, cyclic or linear, in which x and y represent an integer ranging from 0 to 2 and n is greater than or equal to 1, with x+y=2.

Mention may in particular be made, as initiator, of the following compounds:

octa(2-isobutyrylbromide)octa(tert-butyl)calix(8)arene, octa(2-propionylbromide)octa(tert-butyl)calix(8)arene, and hexakis(α-bromomethyl)benzene.

The compound comprising a transition metal which is capable of participating in a reduction stage with the initiator and a "dormant" polymer chain can be chosen from those which correspond to the formula $M^{n+}X'_n$, in which formula:

M can be chosen from Cu, Au, Ag, Hg, Ni, Pd, Pt, Rh, Co, Ir, Fe, Ru, Os, Re, Mn, Cr, Mo, W, V, Nb, Ta and Zn, X' can represent a halogen (in particular bromine or chlorine), OH, (O)$_{1/2}$, an alkoxy radical having 1–6 carbon atoms, (SO$_4$)$_{1/2}$, (PO$_4$)$_{1/3}$, (HPO$_4$)$_{1/2}$, (H$_2$PO$_4$), a triflate, hexafluorophosphate, methanesulphonate, arylsulphonate, SeR, CN, NC, SCN, CNS, OCN, CNO, N$_3$ and R'CO$_2$ radical, in which R represents a linear or branched alkyl or aryl radical having 1–20, preferably 1–10, carbon atoms and R' represents H or a linear or branched alkyl radical having 1–6 carbon atoms or an aryl radical which is optionally substituted by one or more halogen atoms, in particular fluorine and/or chlorine atoms;

n is the charge on the metal.

The choice is preferably made of M representing copper or ruthenium and X' representing bromine or chlorine.

Mention may in particular be made of copper bromide.

Mention may be made, among the ligands capable of being used in the context of the present invention, of compounds comprising at least one nitrogen, oxygen, phosphorus and/or sulphur atom which are capable of coordinating via a σ bond to the compound comprising a transition metal.

Mention may also be made of compounds comprising at least two carbon atoms which are capable of coordinating via a π bond to the compound comprising a transition metal.

Mention may further be made of compounds comprising at least one carbon atom which are capable of coordinating via a σ bond to the compound comprising a transition metal but which do not form a carbon-carbon bond with the monomer during the polymerization, that is to say which do not participate in β-addition reactions with the monomers.

Mention may further be made of compounds capable of coordinating via μ or η bond to the compound comprising a transition metal.

Mention may in particular be made of the compounds of formula:

$$R^9—Z—(R^{14}—Z)_m—R^{10}$$

in which:
$R^9$ and $R^{10}$ are, independently of one another, a hydrogen atom; a linear or branched alkyl radical having 1–20, preferably 1–10, carbon atoms; an aryl radical; a heterocyclyl radical; or an alkyl radical having 1–6 carbon atoms which is substituted with an alkoxy radical having 1–6 carbon atoms or a dialkylamino radical having 14 carbon atoms or a —C(=Y)$R^5$ or —C(=Y)

$NR^6R^7$ and/or $YC(=Y)R^8$ radical (see the definitions $R^5$ to $R^8$ and Y above);

it being given that $R^9$ and $R^{10}$ can be joined so as to form a saturated or unsaturated ring;

$R^{14}$ represents, independently of one another, a divalent group chosen from alkanediyls having 2–4 carbon atoms; alkenylenes having 2–4 carbon atoms; cycloalkanediyls having 3–8 carbon atoms; cycloalkenediyls having 3–8 carbon atoms; arenediyls and heterocyclylenes;

Z represents O, S, $NR^{15}$ or $PR^{15}$, with $R^{15}$ representing H; a linear or branched alkyl radical having 1–20 carbon atoms; an aryl radical; a heterocyclyl radical; or an alkyl radical having 1–6 carbon atoms which is substituted with an alkoxy radical having 1–6 carbon atoms or a dialkylamino radical having 14 carbon atoms or a $—C(=Y)R^5$ or $—C(=Y)NR^6R^7$ and/or $YC(=Y)R^8$ radical (see the definitions of $R^5$ to $R^8$ and Y above);

m is between 0 and 6.

Mention may also be made of the compounds of formula:

in which:

$R^{20}$ and $R^{21}$ are, independently of one another, a hydrogen atom; a halogen atom; a linear or branched alkyl radical having 1–20, preferably 1–10, carbon atoms; an aryl radical; or a heterocyclyl radical; it being given that R20 and $R^{21}$ can be joined so as to form a saturated or unsaturated ring; it being given that, in addition, each radical can be substituted with an alkyl radical having 1–6 carbon atoms, an alkoxy radical having 1–6 carbon atoms or an aryl radical;

$R^5$ and Y being defined above.

Mention may further be made, as ligands, of carbon monoxide; optionally substituted porphyrins and porphycenes; optionally substituted ethylenediamine and propylenediamine; polyamines with tertiary amines, such as pentamethyldiethylenetriamine; aminoalcohols, such as aminoethanol and aminopropanol, which are optionally substituted; glycols, such as ethylene glycol or propylene glycol, which are optionally substituted; arenes, such as benzene, which are optionally substituted; optionally substituted cyclopentadiene; optionally substituted pyridines and bipyridines; acetonitrile; 1,10-phenanthroline; cryptands and crown ethers; or sparteine.

The preferred ligands are chosen in particular from pyridines and bipyridines which are optionally substituted by $C_2$–$C_{15}$ alkyl radicals, in particular $C_6$–$C_{12}$ radicals and especially the nonyl radical; or polyamines with tertiary amines, such as pentamethyldiethylenetriamine.

The polymerization of the monomers, in the presence of the initiator, of the compound comprising a transition metal and of the ligand which acts as activator, results in the production of a polymer having a star structure, which can be represented by the formula (I) given above, in which the monomers have polymerized to give "n" alike or different polymer chains all connected to a polyfunctional centre A which derives from the initiator.

It has been found that, in order to achieve the goal pursued by the present invention, that is to say to obtain a composition which does not exhibit the disadvantages of the prior art and which is in particular comfortable to apply and to wear while making it possible to soften fine lines/wrinkles, it is preferably to choose a polymer corresponding to the following criteria:

it preferably comprises one or more monomers Mi, the corresponding homopolymer of which exhibits a Tg of greater than or equal to approximately 10° C., preferably of greater than or equal to 15° C. and even better still of greater than or equal to 20° C.;

this or these monomers Mi being present in the final polymer in a minimum amount of approximately 45% by weight, preferably in an amount of between 55 and 99% by weight and even better still in an amount of 75–90% by weight with respect to the total weight of monomers.

The polymer may or may not comprise other monomers.

However, it is possible for it to additionally comprise one or more monomers Mj, the corresponding homopolymer of which exhibits a Tg of less than or equal to approximately 10° C., preferably of less than or equal to 5° C and even better still of less than or equal to 0° C.

In this case, this or these monomers Mj are present in the final polymer in a maximum amount of approximately 55% by weight, preferably in an amount of between 1 and 45% by weight and even better still in an amount of 10–25% by weight with respect to the total weight of monomers.

The Tg (glass transition temperature) is measured by DSC (Differential Scanning Calorimetry) according to ASTM Standard D3418-97.

The polymers as defined in the present invention are preferably film-forming or can be rendered film-forming by addition of an additional agent which is able to form a film. The term "film-forming" is understood to mean that the polymer, after application to a substrate and evaporation of the solvent (aqueous or organic), results in a transparent and uncracked film.

Such an additional agent which is able to form a film can be chosen from any compound known to a person skilled in the art as being capable of fulfilling the desired role and can be chosen in particular from plasticizing agents and/or from coalescence agents. Mention may in particular be made, alone or as a mixture, of:

glycols and their derivatives, such as diethylene glycol ethyl ether, diethylene glycol methyl ether, diethylene glycol butyl ether, diethylene glycol hexyl ether, ethylene glycol ethyl ether, ethylene glycol butyl ether or ethylene glycol hexyl ether;

glycerol esters, such as glycerol diacetate (diacetin) and glycerol triacetate (triacetin);

propylene glycol derivatives, in particular propylene glycol phenyl ether, propylene glycol diacetate, propylene glycol methyl ether, propylene glycol ethyl ether, propylene glycol butyl ether, dipropylene glycol methyl ether, dipropylene glycol butyl ether, dipropylene glycol ethyl ether, tripropylene glycol butyl ether or tripropylene glycol methyl ether;

acid esters, in particular carboxylic acid esters, such as citrates, phthalates, adipates, carbonates, tartrates, phosphates or sebacates, oxyethylenated derivatives, such as oxyethylenated oils, in particular vegetable oils, such as castor oil; or oxyethylenated silicone oils.

The amount of additional agent which is able to form a film can be chosen by a person skilled in the art on the basis of his overall knowledge so as to form a film having the desired mechanical properties while retaining, in the composition, cosmetically acceptable properties.

In a preferred embodiment of the invention, a polymer, optionally in combination with additional agents which are able to form a film, is chosen which makes it possible to obtain a film having the following physicochemical characteristic:

a retraction of the isolated stratum corneum of greater than approximately 1%, preferably of greater than or equal to 1.1%, measured using a dermometer, at 30° C., under a relative humidity of 40%, for a concentration of 7% of polymer in a solvent such as isododecane or water.

The film also preferably exhibits a modulus of elasticity (Young's modulus) of between $10^8$ and $9 \times 10^9$ Pa (or N/m$^2$), preferably of between $5 \times 10^8$ and $8.5 \times 10^9$ Pa, preferably of between $10^9$ and $8 \times 10^9$ Pa.

This corresponds to a modulus of elasticity which is greater, preferably at least 10 to 100 times greater, than that of the stratum corneum; the use of a polymer possessing such a Young's modulus makes it possible to obtain both immediate and enduring effectiveness and good comfort in the tightening effect, that is to say without excessive tugging.

The measurement methods are described before the examples.

The pH of the composition is generally in the region of the pH of the skin, that is to say from approximately 5 to approximately 8 and preferably 5.5 to 6.5.

The polymers as define d above can be present in the medium in a form dissolved or dispersed in an aqueous, organic or aqueous/organic phase, in particular an alcoholic or aqueous/alcoholic phase.

The polymers can be present in the composition according to the invention in an amount which can be easily determined by a person skilled in the art according to the application envisaged and which can be between 1–95% by weight, on a dry basis, with respect to the total weight of the composition, preferably between 1.5–90% by weight and preferably between 2–50% by weight.

The compositions, in particular cosmetic compositions, according to the invention therefore additionally comprise a physiologically acceptable medium which can be chosen by a person skilled in the art according to the application envisaged.

This medium can comprise an aqueous phase and/or a fatty phase. It can also be anhydrous.

The aqueous phase can comprise water and/or a thermal water and/or a spring water and/or a mineral water and/or a floral water.

It can also comprise one or more cosmetically acceptable organic solvents or else a mixture of water and of one or more cosmetically acceptable organic solvents. Mention may be made, among these organic solvents, of:

$C_1$–$C_4$ alcohols, such as ethanol, ispropanol or n-propanol;

ethers, such as dimethoxyethane;

ketones, such as acetone or methyl ethyl ketone;

lower $C_1$–$C_3$ carboxylic acid esters, such as methyl acetate or ethyl acetate.

The fatty phase can comprise conventional volatile or non-volatile oils, gums and/or waxes of animal, vegetable, mineral or synthetic origin, alone or as mixtures, in particular:

linear, branched or cyclic, volatile or non-volatile, silicone oils which are optionally organomodified; phenylated silicones; or silicone resins and gums which are liquid at room temperature;

mineral oils, such as liquid paraffin and liquid petrolatum;

oils of animal origin, such as perhydrosqualene or lanolin;

oils of vegetable origin, such as liquid triglycerides, for example sunflower, maize, soybean, jojoba, gourd, grape seed, sesame, hazlenut, apricot, macadamia, avocado, sweet almond or castor oils, triglycerides of caprylic/capric acids, olive oil, groundnut oil, rapeseed oil or coconut oil;

synthetic oils, such as purcellin oil, isoparaffins, fatty alcohols or esters of fatty acids;

fluorinated and perfluorinated oils or fluorinated silicone oils;

waxes chosen from known animal, fossil, vegetable, mineral or synthetic waxes, such as paraffin waxes, polyethylene waxes, carnauba or candelilla waxes, beeswaxes, lanolin wax, chinese insect waxes, rice wax, ouricury wax, esparto wax, cork fibre wax, sugarcane wax, japan wax, sumach wax, montan wax, microcrystalline waxes, ozokerite, the waxes obtained by the Fischer-Tropsch sysnthesis, silicone waxes or their mixtures.

The composition can additionally comprise at least one water-soluble dye and/or at least one pigment which are used conventionally in the field of cosmetics and make-up. The term "pigments" should be understood as meaning white or coloured and inorganic or organic particles which are insoluble in the medium and which are intended to colour and/or opacify the composition. The pigments can be present in the composition in a proportion of 0–20% by weight of the final composition and preferably in a proportion of 1–5%. They can be white or coloured, inorganic and/or organic and conventional or nanometric in size. Mention may be made, among inorganic pigments and nanopigments, of titanium, zirconium or cerium oxides, as well as zinc, iron or chromium oxides or ferric blue. Mention may be made, among organic pigments, of carbon black and barium, strontium, calcium or aluminium lakes. Mention may be made, among water-soluble dyes, of the dyes which are standard in the field under consideration, such as the disodium salt of ponceau, the disodium salt of alizarine, quinoline yellow, the trisodium salt of amaranth, the disodium salt of tartrazine, the monosodium salt of rhodamine, the disodium salt of fuchsine or xanthophyll.

Furthermore, the composition according to the invention can comprise adjuvants commonly used in cosmetic or pharmaceutical compositions intended in particular for a topical application. In particular, these compositions can comprise:

cosmetic and/or pharmaceutical active principles, such as softeners, antioxidants, opacifiers, emollients, hydroxy acids, antifoaming agents, moisturizers, vitamins, fragrances, preservatives, sequestering agents, UV screening agents, ceramides, agents for combating free radicals, slimming agents, bactericides, antidandruff agents, complexing agents, odour absorbers; care active principles, such as agents for combating acne; agents for combating hair loss, antifungal or antiseptic agents, antiperspirants or antibacterials;

fillers, pearlescent agents, lakes, thickeners, gelling agents, polymers, in particular fixing or conditioning polymers, propellants, basifying or acidifying agents, plasticizers or surfactants;

additional hydrophilic polymers, such as poly(vinyl alcohol)s and their copolymers, polysaccharides or cellulose polymers, or natural proteins or synthetic polypeptides;

water-soluble polymers.

Of course, a person skilled in the art will take care to choose this or these optional adjuvants and/or their amounts so that the advantageous properties of the composition according to the invention are not, or not substantially, detrimentally affected by the envisaged addition.

The compositions according to the invention can be provided in various forms and in particular in the form of oil-in-water, water-in-oil or multiple emulsions with a liquid or semi-liquid consistency of the milk type or with a soft, semi-solid or solid consistency of the cream or gel type; of aqueous or oily dispersions or of dispersions in a solvent medium of lotion or serum type; of aqueous, aqueous/alcoholic or oily solutions or of solutions in a solvent medium; of aqueous or oily gels; of microemulsions; of microcapsules; of microparticles or of vesicular dispersions of ionic or non-ionic type; in thickened or gelled fluid form, semi-solid form or soft paste form; or in solid form, such as a stick or tube.

Thus, when the composition of the invention is an emulsion, the proportion of the fatty phase can range from 5 to 80% by weight and preferably from 5 to 50% by weight with respect to the total weight of the composition. The fatty substances, the emulsifiers and the coemulsifiers used in the composition in the emulsion form are chosen from those conventionally used in the field under consideration. The emulsifier and the coemulsifier can be present in the composition in a proportion ranging from 0.3 to 30% by weight and preferably from 0.5 to 20% by weight with respect to the total weight of the composition. Mention may be made, as emulsifiers and coemulsifiers which can be used in the invention, of, for example, polyethylene glycol fatty acid esters, such as PEG-50 stearate and PEG40 stearate, and polyol fatty acid esters, such as glyceryl stearate and sorbitan tristearate.

These compositions can be more or less fluid and can have the appearance of a white or coloured cream, of an ointment, of a milk, of a lotion, of a serum, of a paste or of a foam. They can optionally be applied to the skin in aerosol form. They can also be provided in the solid form.

The compositions according to the invention find an application in particular as cosmetic or pharmaceutical compositions for the skin, mucous membranes, semi-mucous membranes and/or scalp.

They find a very particular application as product for protecting or caring for the skin of the face, of the neck, of the hands or of the body, in particular as a composition for combating wrinkles or tiredness which makes it possible to give a burst of radiance to the skin; it is also possible to envisage an application in the field of compositions for making up the skin of the face or of the body, such as lipsticks, foundations or tinted creams, or antisun or artificial tanning compositions.

The invention is illustrated in more detail in the following examples.

A) Measurement of the Young's Modulus (or Modulus of Elasticity)

The Young's modulus (modulus of elasticity) is measured according to the standard ASTM Standards, Volume 06.01 D 2370-92, "Standard Test Method for Tensile Properties of Organic Coatings".

The film deposited on the substrate must have a thickness of approximately 300 microns before drying. After drying for 7 days at 21° C. and under a relative humidity of 50%, a film is obtained which has a thickness of approximately 100 microns.

The samples measured have a width of 5 mm and a thickness of 100 microns. The distance between the clamping jaws is 25 mm. The tensioning rate is 1000 mm per minute.

B) Retraction Measurement Method

The principle includes measuring, before treatment and after treatment, the length of a test specimen isolated stratum corneum and in determining the percentage of retraction of the test specimen.

Use is made of 1 cm×0.4 cm test specimens of stratum corneum with a thickness ranging from 10 to 20 μm positioned on an MTT 610 extensometer sold by the company Diastron.

The test specimen is placed between 2 jaws and then left for 12 hours in an atmosphere at 30° C. and 40% relative to humidity.

The test specimen is tensioned at a rate of 2 mm/minute by a length of between 5 and 10% of the initial length in order to determine the length $L_1$ from which the test specimen begins to exert a force on the jaws detected by the device.

The test specimen is subsequently relaxed and then 2 mg of an aqueous composition comprising 7% by weight of polymer are applied to the stratum corneum. After complete evaporation of the composition, the test specimen is tensioned under the same conditions as those described above in order to also determine the length $L_2$ for the treated test specimen.

The percentage of retraction is determined by the ratio:

$100 \times (L_2 - L_1)/L_1$.

EXAMPLE 1

Preparation of the Initiator

The initiator prepared was 5,11,17,23,29,35,41,47-octa(2-propionylbromide)-49,50,51,52,53,54,55,56-octa(tert-butyl)calix(8)arene (M=2378 g).

The reactants used were as follows:

| | |
|---|---|
| 4-(tert-butyl)calix(8)arene (M = 1298 g), comprising 8 phenol units (Aldrich) | 15 g |
| 2-bromopropionyl bromide of formula $CH_3$—CHBr—COBr | 59.9 g |
| triethylamine | 28 g |
| tetrahydrofuran (THF) | 120 g |

The 4-(t-butyl)calix(8)arene and the solvent THF were added to a round-bottomed flask equipped with a stirrer and a thermometer; the mixture was left stirring for 10 minutes at room temperature.

The triethylamine was subsequently added, which took approximately 15 minutes.

The 2-bromopropionyl bromide, dissolved beforehand in THF, was then added at a temperature of approximately 5° C., which took approximately 1 h 30.

The mixture was left stirring for at least 12 hours at 5° C. and then the temperature was allowed to gradually rise to room temperature.

The solution obtained was concentrated by evaporating the THF. A product was precipitated from a water/ice mixture, extraction was then carried out with ethyl ether and the extract was dried over magnesium sulphate.

The solution obtained was concentrated and a compound was precipitated from a methanol/ice (90/10) mixture in a compound/precipitant ratio of 1/5.

23 g of compound were obtained, i.e., a yield of 85%, which compound existed in the form of a powder.

Characterization was carried out by NMR/GC or HPLC. The compound obtained exhibited values in accordance with those expected.

EXAMPLE 2

Preparation of an 8-Branched Star Polymer, Each Branch of Which was a Block Copolymer 1) First Stage: Preparation of a Star Polymer With 8 Poly (isobutyl Methacrylate) Branches The reactants used were as follows:

| | |
|---|---|
| monomer 1: isobutyl methacrylate (Tg = 53° C.) | 105 g |
| monomer 2: butyl acrylate (Tg = −50° C.) | 15 g |
| initiator (prepared according to Example 1) (corresponding to 4 × 10$^{-3}$ mol of RBr) | 1.19 g |
| CuBr (corresponding to 4 × 10$^{-3}$ mol) | 0.57 g |
| Bipyridine (corresponding to 8 × 10$^{-3}$ mol) | 1.25 g |

The monomers were distilled beforehand.

The reactants, except the monomers, were mixed in a sealed and flame-treated reactor comprising a nitrogen inlet and then the monomer 1 was added.

The reactor was heated under nitrogen to approximately 120° C. and reaction was then allowed to take place at 120° C. for 4 hours, the nitrogen inlet being disconnected.

2) Second Stage: Formation of the Second Block at the End of Each Branch

The monomer 2 was then added and reaction was again allowed to take place at 120° C. for 4 hours.

After reaction, the reaction mixture was allowed to cool; a viscous green solution was obtained, which solution was dissolved in dichloromethane. The polymer solution was passed through neutral alumina and the clear solution obtained was precipitated from a methanol/water (80/20) mixture in a polymer/precipitant ratio of 1/5.

95 g of polymer were obtained, i.e., a yield of 95%, which polymer existed in the form of a viscous product.

This polymer was a star polymer with 8 poly(isobutyl methacrylate) branches, each branch of which was a block copolymer: calix(poly(isobutyl methacrylate)-block-poly (butyl acrylate)).

Characterization was carried out by GC:THF linear polystyrene equivalent, light scattering detection: 304,000 g/mol (theoretical mass: approximately 240,000); polydispersity index: 1.38.

The polymer obtained exhibited values in accordance with those expected.

Retraction of the stratum corneum: 1.1%.

EXAMPLE 3

Serum for Combating Wrinkles

A serum to be applied to the neck and face was prepared comprising:

| | |
|---|---|
| polymer of Example 2, as a 7% by weight solution in isododecane | 100% |

A serum was obtained which was easily applied to the skin.

What is claimed is:

1. A process for treating a keratinous substance, comprising applying to said keratinous substance a composition, comprising, in a physiologically acceptable medium, at least one polymer having a star structure chosen from structures of formula (I):

$$A-[(M1)_{p1}-(M2)_{p2}\ldots(Mi)_{pj}]_n \qquad (I)$$

in which:

A is chosen from polyfunctional centers having a functionality n;

$[(M1)_{p1}-(M2)_{p2}\ldots(Mi)_{pj}]$ represents a branch comprising at least one polymerized monomeric unit Mi having a polymerization index pj;

n is an integer greater than or equal to 2;

pj is greater than or equal to 2;

there are at least two branches, which may be identical or different; and said at least two branches are grafted covalently to A; and wherein said at least one polymerized monomeric unit Mi comprised by at least one of said at least two branches is chosen from polymerized monomeric units Mk, which may be identical or different, wherein a homopolymer formed by the corresponding polymerized monomeric units Mk has a Tg of greater than or equal to 10° C.; and wherein said at least one polymerized monomeric unit Mi chosen from polymerized monomeric units Mk is present in an amount ranging from 45 to 99 percent by weight relative to the total weight of the polymerized monomeric units Mi.

2. A process according to claim 1, further comprising at least one polymerized monomeric unit Mi contained by at least one of said at least two branches chosen from polymerized monomeric units Mj, which may be identical or different, wherein a homopolymer formed by the corresponding polymerized monomeric units Mj has a Tg of less than or equal to 10° C.; and wherein said at least one polymerized monomeric unit Mi chosen from polymerized monomeric units Mj is present in an amount less than or equal to 55 percent by weight relative to the total weight of the polymerized monomeric units Mi.

3. A process according to claim 1, further comprising at least one film-forming agent.

4. A process according to claim 1, wherein said keratinous substance is chosen from skin from the face, neck, hands, and/or body.

5. A process according to claim 1, wherein said keratinous substance is chosen from human keratinous substances.

6. A process for cosmetic treatment of wrinkles or fine lines of skin, comprising applying to said wrinkles or fine lines at least one polymer in an amount effective for softening the wrinkle or fine line by producing a tightening effect, wherein said at least one polymer having a star structure chosen from structures of formula (I):

$$A-[(M1)_{p1}-(M2)_{p2}\ldots(Mi)_{pj}]_n \qquad (I)$$

in which:

A is chosen from polyfunctional centers having a functionality n;

$[(M1)_{p1}-(M2)_{p2}\ldots(Mi)_{pj}]$ represents a branch comprising at least one polymerized monomeric unit Mi having a polymerization index pj;

n is an integer greater than or equal to 2;

pj is greater than or equal to 2;

there are at least two branches, which may be identical or different; and said at least two branches are grafted covalently to A; and wherein said at least one polymerized monomeric unit Mi comprised by at least one of said at least two branches is chosen from polymerized monomeric units Mk, which may be identical or different, wherein a homopolymer formed by the corresponding polymerized monomeric units Mk has a Tg of greater than or equal to 10° C.; and wherein said at least one polymerized monomeric unit Mi chosen from polymerized monomeric units Mk is present in an amount ranging from 45 to 99 percent by weight relative to the total weight of the polymerized monomeric units Mi.

7. A process according to claim 6, further comprising at least one polymerized monomeric unit Mi contained by at least one of said at least two branches chosen from polymerized monomeric units Mj, which may be identical or different, wherein a homopolymer formed by the corresponding polymerized monomeric units Mj has a Tg of less than or equal to 10° C.; and wherein said at least one polymerized monomeric unit Mi chosen from polymerized monomeric units Mj is present in an amount less than or equal to 55 percent by weight relative to the total weight of the polymerized monomeric units Mi.

8. A process according to claim 6, further comprising at least one film-forming agent.

* * * * *

UNITED STATES PATENT AND TRADEMARK OFFICE
CERTIFICATE OF CORRECTION

PATENT NO. : 6,692,733 B1
DATED : February 17, 2004
INVENTOR(S) : Nathalie Mougin It is certified that error appears in the above-identified patent and that said Letters Patent is hereby corrected as shown below:

Title page,
Item [57], delete the ABSTRACT in its entirety and insert the following:

--Polymer having a star structure chosen from structures of formula (I):

$$A\text{-}[(M1)_{p1}\text{-}(M2)_{p2}\ldots(Mi)_{pj}]_n \quad (I)$$

in which:

A is chosen from polyfunctional centers having a functionality n;

$[(M1)_{p1}\text{-}(M2)_{p2}\ldots(Mi)_{pj}]$ represents a branch comprising at least one polymerized monomeric unit Mi having a polymerization index pj;

n is an integer greater than or equal to 2;

i is greater than or equal to 1;

pj is greater than or equal to 2;

the at least two branches may be identical or different; and the at least two branches are grafted covalently to A;

wherein the at least one polymerized monomeric unit Mi comprised by at least one of said at least two branches is chosen from polymerized monomeric units Mk, which may be identical or different, wherein a homopolymer formed by the corresponding polymerized monomeric units Mk has a Tg of greater than or equal to 10°C; and

UNITED STATES PATENT AND TRADEMARK OFFICE
CERTIFICATE OF CORRECTION

PATENT NO. : 6,692,733 B1
DATED : February 17, 2004
INVENTOR(S) : Nathalie Mougin It is certified that error appears in the above-identified patent and that said Letters Patent is hereby corrected as shown below:

Item [57], ABSTRACT, cont'd, wherein the at least one polymerized monomeric unit Mi chosen from polymerized monomeric units Mk is present in an amount greater than or equal to 45 percent by weight relative to the total weight of the polymerized monomeric units Mi, compositions, and processes containing the polymer are discussed.--.

Signed and Sealed this

Eleventh Day of May, 2004

JON W. DUDAS
*Acting Director of the United States Patent and Trademark Office*